United States Patent [19]

Verheyden et al.

[11] Patent Number: 4,621,140

[45] Date of Patent: Nov. 4, 1986

[54] PROCESS FOR PREPARING 2,6-SUBSTITUTED-9-(1,3-DIHYDROXY-2-PROPOXYMETHYL)-PURINES AND CERTAIN DERIVATIVES

[75] Inventors: Julien P. H. Verheyden, Los Altos; John C. Martin, Redwood City; Daniel P. C. McGee, Mountain View, all of Calif.

[73] Assignee: Syntex (U.S.A.) Inc., Palo Alto, Calif.

[21] Appl. No.: 582,696

[22] Filed: Feb. 23, 1984

[51] Int. Cl.[4] .................. C07D 473/18; A61K 31/52
[52] U.S. Cl. .................................... 544/276; 544/277
[58] Field of Search ............... 544/277, 276; 424/251, 424/253; 514/261

[56] References Cited

U.S. PATENT DOCUMENTS 4,423,050 12/1983 Verheyden et al. ............... 424/253

Primary Examiner—Nicholas S. Rizzo
Attorney, Agent, or Firm—Annette M. Moore; Tom M. Moran

[57] ABSTRACT

Process and novel intermediates for preparing 9-(1,3-dihydroxy-2-propoxymethyl)guanine and 2,6-diamino-9-(1,3-dihydroxy-2-propoxymethyl)purine and certain esters thereof. The present process and intermediates reduce the number of reaction steps to prepare these compounds as compared to prior processes. The products are useful as antiviral agents.

92 Claims, No Drawings

PROCESS FOR PREPARING 2,6-SUBSTITUTED-9-(1,3-DIHYDROXY-2-PROPOXYMETHYL)-PURINES AND CERTAIN DERIVATIVES

BACKGROUND OF THE INVENTION

1. Field of the Invention

This invention relates to a process for preparing 2,6-substituted -9-(1,3-dihydroxy-2-propoxymethyl)purines and certain esters thereof. The invention also relates to novel intermediates useful in the above process and to a process for preparing these intermediates.

2. Related Disclosure

The compounds 9-(1,3-dihydroxy-2-propoxymethyl)-guanine and 2,6-diamino-9-(1,3-dihydroxy-2-propoxymethyl)-purine and certain esters thereof are potent antiviral agents and have been prepared by methods disclosed in U.S. Pat. No. 4,355,032 and European patent applications 49,072; 72,027 and 74,306. The present invention relates to an improved process whereby the side chain intermediate is more stable than known intermediates and is prepared in less steps. One embodiment of the instant invention also eliminates the costly and time consuming hydrogenation step for removal of the protecting benzyl groups from the hydroxy groups on the side chain. Another embodiment of the present invention avoids the chloromethylation step of the known process which yields, as a by-product, bis-chloromethylether, a known carcinogen. The invention also relates to the novel intermediates and to a method of preparing them.

SUMMARY OF THE INVENTION

The first aspect of the invention is a process for preparing 9-(1,3-dihydroxy-2-propoxymethyl)guanine and 2,6-diamino-9-(1,3-dihydroxy-2-propoxymethyl)purine and certain esters thereof as depicted by the following reaction sequence:

REACTION SEQUENCE

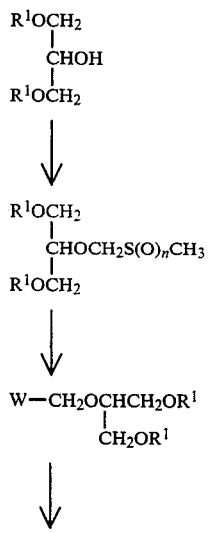

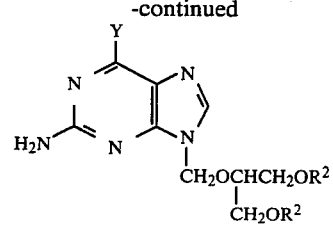

(I)

wherein $R^1$ is a removable group, $R^2$ is hydrogen or a sterically hindered acyl group, Y is amino or hydroxy, W is an appropriately substituted purine group and n is 0 or 1.

Another aspect of the invention are the novel intermediates of the formula

wherein $R^1$ is a sterically hindered group or $R^5C(O)$ wherein $R^5$ is alkyl or optionally substituted phenyl or the two $R^1$'s together are $ZZ^1C<$ wherein Z is optionally substituted phenyl and $Z^1$ is hydrogen or Z and $Z^1$ are both methyl;

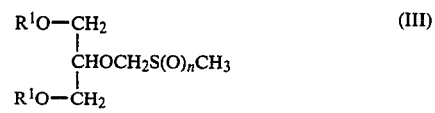

wherein $R^1$ is a sterically hindered group, an optionally substituted benzyl group or $R^5C(O)$ wherein $R^5$ is alkyl or optionally substituted phenyl or the two $R^1$'s together are $ZZ^1C<$ wherein Z is optionally substituted phenyl and $Z^1$ is hydrogen or Z and $Z^1$ are both methyl and n is 0 or 1, and

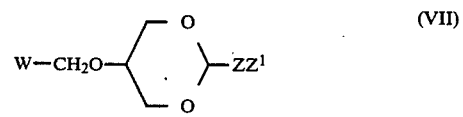

wherein W is a protected guanine, 2-amino-6-chloropurine or 2,6-dichloropurine; and Z is optionally substituted phenyl and $Z^1$ is hydrogen or Z and $Z^1$ are both methyl.

Yet another aspect of the invention is a process for preparing the novel intermediates of formula (III).

DETAILED DESCRIPTION AND PREFERRED EMBODIMENTS

As used in the specification and appended claims, unless specified to the contrary, the following terms have the meaning indicated.

The term "alkyl" refers to a straight or branched chain monovalent substituent consisting solely of carbon and hydrogen, containing no unsaturation and having one to nineteen carbon atoms. Examples of alkyl are methyl, n-butyl, 2-methyl-2-propyl n-octyl, n-decyl, n-tetradecyl and n-nonadecyl. The term "lower alkyl" refers to alkyl groups as defined above but containing one to six carbon atoms. The term "1-adamantyl" refers to the following ring structure.

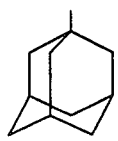

"Lower alkoxy" refers to "lower alkyl-O-" wherein "lower alkyl" is as defined above. Examples of "lower alkoxy" are methoxy, ethoxy, i-butoxy and n-hexyloxy. "Acyl" refers to the group RC(O) wherein R is a lower alkyl group, $R^5$ or a sterically hindered alkyl group. Examples of "acyl" are acetyl, propanoyl, n-butanoyl and 2,2-dimethylpropanoyl. "Optionally substituted" refers to substitution on a phenyl ring with one or two lower alkyl or lower alkoxy.

The term "hydrogen donor" refers to a substance which generates hydrogen ions. Examples of hydrogen donors are hydrogen gas, cyclohexene, 1,4-cyclohexadiene and the like.

"Removable groups" refers to any group which may be removed by hydrolysis or hydrogenation. Examples of "removable groups" useful in the present invention are
  (a) sterically hindered groups;
  (b) optionally substituted benzyl;
  (c) $R^5C(O)$ wherein $R^5$ is alkyl or optionally substituted phenyl; and
  (d) $ZZ^1C<$ wherein Z is optionally substituted phenyl and $Z^1$ is hydrogen or Z and $Z^1$ are both methyl.

The term "sterically hindered group" refers to a group derived from a reagent which selectively reacts with the primary hydroxy groups of glycerol. Examples of "sterically hindered groups" are
  (i) sterically hindered acyl groups such as 1-adamantylcarbonyl and

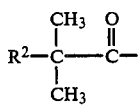

wherein $R^2$ is alkyl of one to twelve carbon atoms;
  (ii) sterically hindered silyl groups of the formula $R_3^3$-Si wherein $R^3$ is independently optionally substituted phenyl, optionally substituted benzyl or an alkyl of one to twelve carbon atoms with the proviso that if all three $R^3$'s are alkyl at least one must be branched on the carbon alpha to the silicon atoms; and
  (iii) diphenylmethyl and triphenylmethyl (trityl).

The term "removable group precursor" refers to a reagent which upon reaction yields the group $R^1$ wherein $R^1$ is as defined supra. Examples of "removable group precursor" are sterically hindered acyl chlorides, $R^5C(O)Cl$, sterically hindered silyl chlorides and the like.

It is understood that the definition of Y as "hydroxy" is meant to encompass the tautomeric oxo form as well.

The process of the present invention is depicted in the Reaction Sequence shown below.

REACTION SEQUENCE

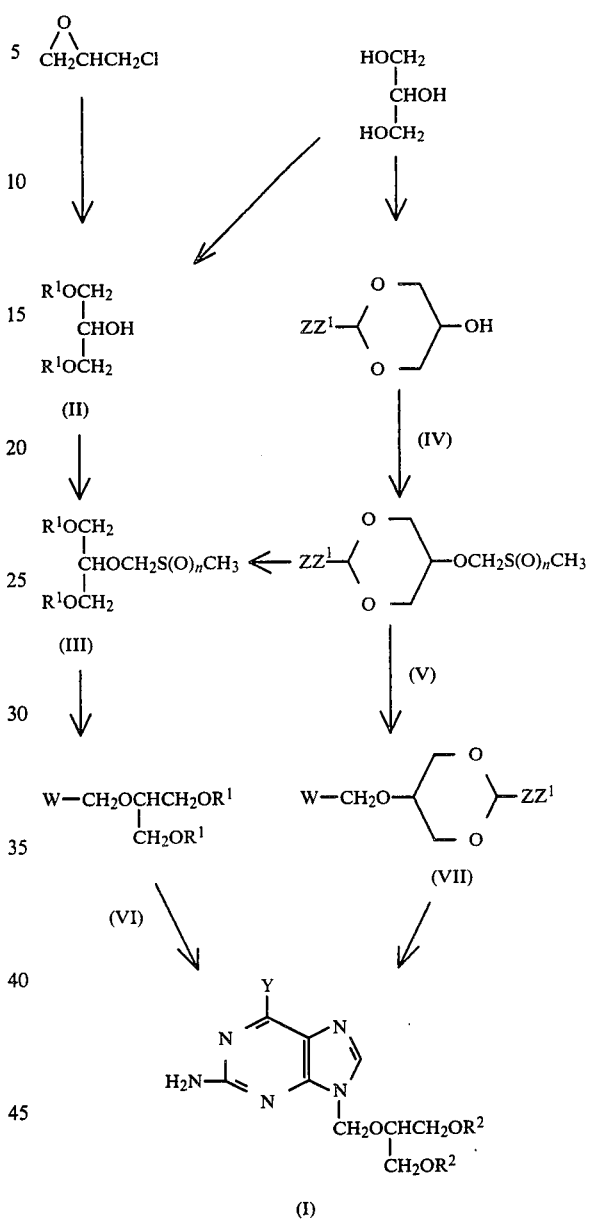

wherein $R^1$ is a removable group as is defined above, $R^2$ is hydrogen or a sterically hindered acyl group, Y is amino or hydroxy, Z is optionally substituted phenyl and $Z^1$ is hydrogen or Z and $Z^1$ are both methyl, W is a protected purine group and n is 0 or 1.

A detailed depiction of the reaction sequence of the present invention is set out above. For clarity the appropriate compounds wherein the two $R^1$'s together are $ZZ^1C<$ are specifically represented, i.e., compounds of formulae (IV), (V) and (VII).

Compounds of formula (II) are prepared by reacting glycerol or epichlorohydrin with a removable group precursor as is described below.

Compounds of formula (II) wherein $R^1$ is a sterically hindered group, i.e., $R_a^1$ may be prepared by reacting glycerol with the appropriate reagent. For example, when $R_a^1$ is a sterically hindered acyl group such as 1-adamantylcarbonyl or 2,2-dimethylpropanoyl, glycerol is reacted with the appropriate acyl chloride. Glycerol dissolved in a solvent such as pyridine, dichloromethane/pyridine, toluene/pyridine, and the like, preferably pyridine, is cooled to $-20°$ C. to $15°$ C., preferably to $-15°$ C. to $10°$ C. using methanol/dry ice bath. The acyl chloride, in a molar ratio of 2–3:1 to glycerol, preferably 2.5:1, is added slowly over ½ hour to two hours, preferably over one hour. The reaction mixture is allowed to warm up to room temperature and is maintained at this temperature for ½ hour to two hours, preferably for 45 minutes to 1½ hours. The compound of formula (II) is extracted and purified by, e.g., chromatography.

The acyl chlorides are readily available from, i.a., Aldrich Chemical Co. or may be prepared by reacting the corresponding acid with a chlorinating agent such as phosphorus trichloride, phosphorus pentachloride or thionyl chloride under reaction conditions well-known in the art.

Compounds of formula (II) wherein $R_a{}^1$ is a sterically hindered silyl group such as t-butyldiphenylsilyl, tribenzylsilyl, t-butyldimethylsilyl and triphenylsilyl may be prepared by reacting glycerol with the appropriate tri(hydrocarbon)silyl reagent such as a tri(hydrocarbon)silyl chloride, hexahydrocarbon silazane, bis[tri(hydrocarbon)silyl]acetamide, tri(hydrocarbon)silyldiphenylurea, bis[tri(hydrocarbon)silyl]urea, tri(hydrocarbon)silylimidazole and the like. Glycerol is reacted with the silyl reagent, either neat or in an aprotic solvent such as dimethylformamide, hexane, acetonitrile, tetrahydrofuran, toluene, dimethylacetamide, N-methylpyrrolidine and the like at room temperature or with heating optionally with reflux for ¼ to 8 hours, the temperature being dependent on the reagent used. For example, the above compound and a tri(hydrocarbon)silyl chloride dissolved in a solvent such as dimethylformamide, dimethylacetamide, N-methylpyrrolidine, and the like are stirred at room temperature for ½ to 5 hours, preferably for ½ to 1½ hours. The reaction is run in the presence of a catalyst, such as triethylamine, tributylamine, pyridine or imidazole with imidazole being preferred.

The silyl reagents are readily available from, i.a., Petrach System, Inc. or if not readily available may be prepared by methods well-known in the art such as the reaction of silicon tetrachloride with the appropriate Grignard reagent or with the appropriate hydrocarbon lithium compound. See, for example, *Organosilicon Compounds,* C. Eaborn (1960).

Compounds of formula (II) wherein $R_a{}^1$ is the diphenylmethyl or trityl group may be prepared by reacting glycerol with diphenylmethyl or triphenylmethyl chloride (trityl chloride). The chlorides are readily available from, i.a., Aldrich Chemical Co. The reactants in a solvent such as dimethylformamide-triethylamine, pyridine, and the like with a catalyst, e.g. 4-dimethylaminopyridine are heated at $40°$ C. to $70°$ C., preferably at $45°$ C. to $60°$ C. for 8 to 24 hours, preferably for 12 to 18 hours.

The compound of formula (II) wherein $R^1$ is optionally substituted benzyl, i.e., $R_b{}^1$ is prepared by adding epichlorohydrin dropwise to a solution of an alkali metal salt, preferably the sodium salt, of an optionally substituted benzyl alcohol is a solvent such as dimethylformamide, dimethylacetamide, hexamethylphosphoramide, dimethylsulfoxide, sulfolane, tetrahydrofuran, and dioxane at a temperature of about $0°$ C. to $100°$ C., preferably at about $15°$ C. to $40°$ C. The reaction mixture is stirred from about 10 hours to 24 hours, preferably from about 12 hours to 18 hours at a temperature of about $0°$ C. to $100°$ C., preferably from about $20°$ C. to $50°$ C.

Compound of formula (III) wherein $R^1$ is $R_a{}^1$ or $R_b{}^1$ is prepared by reacting the compound of formula (II) with a disubstituted sulfoxide such as a methylphenylsulfoxide, dimethylsulfoxide and the like, preferably dimethylsulfoxide (DMSO) in the presence of an organic acid/anhydride mixture such as acetic acid/acetic anhydride. The reaction mixture is stirred at room temperature for 24 to 72 hours, preferably for 36 to 60 hours, extracted with an organic solvent such as dichloromethane, toluene, ethyl acetate, and the like, followed by evaporation and purified by distillation.

Compound of formula (V), i.e., compound of formula (III) wherein the two $R^1$'s together are $ZZ^1C<$, is prepared by reacting glycerol with acetone or an optionally substituted benzaldehyde to form compound of formula (IV) in the presence of a catalytic amount of a strong acid such as sulfuric acid. This mixture is heated to $85°$ C. to $120°$ C., preferably from $90°$ C. to $100°$ C., for ½ hour to three hours, preferably from ¾ hour to 1½ hours. Compound of formula (IV) is reacted with a disubstituted sulfoxide such as DMSO in an organic acid/anhydride mixture such as glacial acetic acid/acetic anhydride and stirred at room temperature for 3 to 7 days, preferably for 4 to 6 days to form compound of formula (V).

The acetal ring of compound of formula (V) may be hydrolyzed with an acid and then reacted with an appropriate acid chloride in the presence of pyridine and the like to form compound of formula (III) wherein $R^1$ equals $R_c{}^1$ and is $R^5C(O)$.

Compounds of formulas (III) or (V) wherein n is 1 are prepared by oxidizing the compounds wherein n is 0 with an oxidizing agent such as sodium hydrochlorite or a peroxy acid such as peroxyacetic acid, peroxybenzoic acid and the like.

Compounds of formula (VI) are prepared from compounds of formula (III) by forming a slurry of compound of formula (III) and the protected purine in admixture with dimethylsulfoxide and an acid such as aluminum chloride, p-toluenesulfonic acid, mercuric chloride, phosphoric acid and the like, preferably aluminum chloride in a solvent such as dimethylformamide. The slurry is heated from $70°$ C. to $150°$ C., preferably from $75°$ C. to $90°$ C. for 2 to 8 hours, preferably from 3 to 5 hours. The cooled mixture is dissolved in an organic solvent such as xylene, extracted and evaporated. The resulting oil is dissolved in a organic solvent such as carbon tetrachloride and the crude precipitate is recovered by filtration. The crude precipitate is recrystallized and compound of formula (VI) is recovered as a solid.

Another method for preparing compound of formula (VI) wherein W is protected 2-amino-6-chloropurine is reacting compound of formula (VI) wherein W is protected guanine with phosphorousoxychloride. The 6-hydroxy group is replaced by chloro.

Compounds of formula (VII) may be prepared by reacting the protected purines with compound of formual (V). A slurry of compound of formula (V), the protected purine in admixture with dimethylsulfoxide and an acid such as aluminum chloride, p-toluenesulfonic acid, mercuric chloride, phosphoric acid and the like, preferably aluminum chloride in a solvent such as dimethylformamide is heated to $60°$ C. to $150°$ C., preferably to 85° C. to 110° C. for 2 to 120 hours, preferably from 24 to 48 hours. The cooled mixture is extracted and compound of formula (VII) is recovered by filtration.

The appropriately substituted purine compound may be guanine available from i.a., Pharma-Waldhof, 2,6-dichloropurine and 2-amino-6-chloropurine available from, i.a, Aldrich Chemical Co. The choice of the purine depends on the desired Y.

Before reaction with compounds of formula (III) or (V) the purines may be protected with acyl or silyl groups.

For example, the protected purine compounds are prepared by heating the purine with acetic anhydride, neat, at reflux for about 10 to 24 hours, preferably for about 12 to 18 hours.

Another method for preparing the acyl protected purine involves reacting the purine with an acid anhydride, preferable acetic anhydride in a solvent such as dimethylformamide in the presence of dimethylaminopyridine and refluxing.

The purine compound may be protected with silyl groups using the reagents and reaction conditions described above for the preparation of compounds of formula (II).

REMOVAL OF THE $R^1$ GROUPS

The $R^1$ groups are removed from compounds of formula (VI) by acidic or basic hydrolysis or by reaction with a hydrogen donor depending on the nature of $R^1$. When $R^1$ is an acyl group basic hydrolysis is preferred. Compound of formula (VI) is reacted with a base such as sodium hydroxide, sodium methoxide, ammonia, ammonium hydroxide and the like. For example, compound of formula (VI) is dissolved in a 50% solution of ammonium hydroxide in methanol. This solution is allowed to stand at room temperature for 5 to 14 days, preferably from 7 to 10 days.

When $R^1$ is a sterically hindered group such as a silyl, diphenylmethyl or trityl group, the groups are removed by acid hydrolysis with acids such as acetic acid, dilute hydrochloric acid and the like.

The optionally substituted benzyl protecting groups are removed from compound of formula (VI) by catalytic hydrogenation or by transfer hydrogenation. A catalyst such as palladium on carbon in a slurry is added to a solution of compound of formula (VI) dissolved in a solvent such as aqueous methanol. Hydrogen is added to the solution at a pressure of 15 psi to 200 psi, preferably at a pressure of 30 psi to 80 psi.

The benzyl groups may be removed by transfer hydrogenation by reaction with cyclohexane, 1,4-cyclohexadiene and the like at atmospheric pressure.

The acetal protecting group of compound of formula (VII) is hydrolyzed to form compound of formula (VIIa) with aqueous acetic acid. The solution is heated to 50°-100° C., preferably from 55°-75° C. for 1 to 4 days, preferably for 1½ to 3 days.

PREPARATION OF COMPOUNDS OF FORMULA (I)

Compounds of formula (I) wherein $R^2$ is hydrogen are prepared from compounds of formula (VI) or (VII) by (1) removal of the $R^1$ groups or hydrolysis of the acetal group, (2) removal of the protecting groups on the purine ring and, if appropriate, (3) conversion of the 6-chloro group to the desired Y and/or the 2-chloro group to the 2-amino group on the purine ring. The above steps may be performed in any sequence or simultaneously as is discussed infra.

Compounds of formula (I) wherein Y is hydroxy may be prepared from compounds of formula (VI) wherein W is protected guanine or protected 2-amino-6-chloropurine. When W is acyl protected guanine and $R^1$ is an acyl group, compound of formula (I) is prepared in a one step reaction using a base such as methanolic ammonia or methanolic ammonium hydroxide as is described above which removes both the $R^1$ groups and the acyl protecting groups. When $R^1$ is silyl, diphenylmethyl or triphenylmethyl a two step process is required. The $R^1$ groups may be removed first by acid hydrolysis or hydrogenation followed by the removal of the acyl protecting groups. It is preferred to first remove the acyl groups on the guanine ring by basic hydrolysis followed by removal of $R^1$. If the guanine ring is protected by silyl groups these groups are removed by acid hydrolysis.

When W is protected 2-amino-6-chloropurine, compound of formula (I) wherein Y is hydroxy is prepared by basic hydrolysis using a strong base such as sodium hydroxide. When $R^1$ is an acyl group the compound is prepared in a one step reaction with the conversion of the 6-chloro group to the 6-hydroxy group and the simultaneous removal of $R^1$. When $R^1$ is other than acyl the groups are removed as discussed supra.

Compounds of formula (I) wherein Y is amino are prepared from compounds of formula (VI) wherein W is a protected 2-amino-6-chloro purine or 2,6-dichloropurine. When $R^1$ is acyl, compound of formula (I) is prepared in a one step basic hydrolysis wherein the 6-chloro group is replaced by an amino group. When $R^1$ is other than acyl the groups are removed as is discussed above. These groups may be removed first followed by replacement of chloro by amino but it is preferred that the chloro is replaced first followed by removal of $R^1$.

When W is 2,6-dichloropurine, the 6-chloro is replaced by amino under the basic hydrolysis reaction conditions using ammonia or ammonium hydroxide discussed above. The 2-chloro group is replaced by an amino group under more stringent conditions such as using methanolic ammonia in a bomb. The $R^1$ groups are removed as is discussed above.

The hydrolyzed form of compound of formula (VII), i.e., compound of formula (VIIa) is converted to compound of formula (I) by removal of the protecting groups on the purine ring and/or the conversion of the chloro groups by the methods discussed above.

Compounds of formula (I) wherein $R^2$ is a sterically hindered acyl group are prepared under mild reaction conditions from compounds of formula (VI) wherein W is an acyl protected guanine or 2-amino-6-chloropurine and $R^1$ is a sterically hindered acyl group. For example, compounds of formula (VI) as is defined above in a 5-20% solution, preferably and 8-12% solution, of ammonia in methanol is maintained at room temperature for 4 to 12 hours, preferably for 6 to 8 hours. The compounds of formula (I) are recovered by crystallization. The compounds may also be prepared by using more concentrated basic solutions for a shorter period of time and/or at lower reaction temperatures.

A preferred embodiment of the present invention comprises a process for preparing the compound of formula (I) wherein Y is a hydroxy group. Within this embodiment it is preferred that $R^2$ is hydrogen.

Another preferred embodiment of the instant invention comprises a process whereby the protecting groups on the purine ring and the $R^1$ are removed by hydrolysis with basic hydrolysis being particularly preferred. Within this embodiment it is preferred that the basic hydrolysis is accomplished with a methanolic solution of ammonia or ammonium hydroxide. It is further preferred that the protecting groups on the purine ring and the $R^1$ groups are removed simultaneously.

Particularly preferred $R^1$ groups are selected from the group consisting of sterically hindered acyl and $R^5C(O)$ wherein $R^5$ is as defined above. Particularly preferred is 2,2-dimethylpropanoyl.

It is also preferred that W is a protected guanine ring or a protected 2-amino-6-chloropurine ring. It is especially preferred that the protecting groups are acyl with acetyl being most preferred.

The following specific examples are illustrative of the present invention and should not be considered as limitative thereof.

PREPARATION I (Preparation of compound of formula II wherein $R^1$ is 2,2-dimethylpropanoyl)

To a pyridine (100 ml) solution containing glycerol (10 gm) chilled in a methanol/dry ice bath 33.25, ml of 2,2-dimethylpropanoylchloride was slowly added over one hour. The reaction mixture was maintained at $-10°$ C. for one hour, followed by one hour at room temperature. Methanol (30 ml) was added and the resultant mixture was evaporated to a small volume and then partitioned between dichloromethane and 6% NaHCO$_3$. The organic phase was washed with water, dried (Na$_2$SO$_4$) and evaporated to give a light yellow oil (26 gm). The oil was purified by chromatography (dichloromethane) to give 20 gm of 1,3-di-O-(2,2-dimethylpropanoyl)glycerol as an oil.

PREPARATION II (Preparation of compound of formula (III) wherein $R^1$ is 2,2-dimethylpropanoyl)

A solution of 1,3-di-O-(2,2-dimethylpropanoyl)glycerol (26 gm), dimethylsulfoxide (100 ml) dried over molecular sieve, acetic acid (60 ml) and acetic anhydride (50 ml) was stirred at room temperature for 48 hours. The resultant reaction mixture was diluted with dichloromethane and then washed with water (3X). Alternatively, the mixture may be diluted with toluene. The organic phase was dried (Na$_2$SO$_4$) and evaporated to give a yellow oil. Fractional distillation (116° C.–120° C./0.5 torr) gave 9.8 gm of 1,3-di(2,2-dimethylpropanoyloxy)-2-propoxymethylthiomethane as an oil.

PREPARATION III (Preparation of compound of formula (VI) wherein $R^1$ is 2,2-dimethylpropanoyl)

A slurry of 1,3-di(2,2-dimethylpropanoyloxy)-2-propoxymethylthiomethane (1 gm), diacetylguanine:DMSO (734 mg), AlCl$_3$ (166 mg) and dimethylformamide (1 ml) was heated at 80° C. for 3½ hours, then cooled and dissolved in dichloromethane. The organic phase was washed with water (IX), dried (Na$_2$SO$_4$) and evaporated to a brown oil. Trituration of the oil in carbon tetrachloride and filtration of the resulting precipitate gave crude N$^2$-acetyl-9-(1,3-di(2,2-dimethylpropanoyloxy)-2-propoxymethyl)guanine, 629 mg, which was recrystallized from ethyl acetate/hexane to give N$^2$-acetyl-9-(1,3-di(2,2-dimethylpropanoyloxy)-2-propoxymethyl)guanine, 484 mg, as a white solid, m.p. 192°–193° C.

PREPARATION IV

A solution of N$^2$-acetyl-9-[1,3-di(2,2-dimethylpropanoyloxy)-2-propoxymethyl]]guanine prepared in Preparation III. (2.98 g), tetraethylammonium chloride (2.92 g), N,N-dimethylaniline (1.12 ml), phosphorousoxychloride (4.79 ml), in acetonitrile (25 ml) was heated at reflux under anhydrous conditions for 10 minutes then evaporated. The residue was chromatographed (1:15 methanol/dichloromethane chloride) to give 2.15 g of N$^2$-acetyl-2-amino-6-chloro-9-[1,3-di(2,2-dimethylpropanoyloxy)-2-propoxymethyl]]purine. Recrystallization from ethyl acetate/hexane yielded 1.25 g of N$^2$-acetyl-2-amino-6-chloro-9-[1,3-di(2,2-dimethylpropanoyloxy)-2-propoxymethyl]purine: mp 122°–123° C.

PREPARATION V

To a solution of 22.8 g of 1,3-di(2,2-dimethylpropanoyloxy)-2-propoxymethylthiomethane in 300 ml of dichloromethane was added peroxyacetic acid until only a faint trace of the sulfide was detectable by TLC. The resultant solution was washed with 100 ml of sodium thiosulfate, 200 ml of aqueous sodium hydrogen carbonate, 100 ml of sodium thiosulfate and 100 ml of water. The organic phase was dried over sodium sulfate and evaporated. The residue was chromatographed over 500 g silica gel using ethyl acetate as eluent. 1,3-Di(2,2-dimethylpropanoyloxy)-2-propoxymethylsulfinylmethane (8.84 g) was recovered as a clear oil.

PREPARATION VI (Preparation of compound of formula (IV))

A mixture of glycerol (220 g), benzaldehyde (200 g) and concentrated sulfuric acid (10 drops) was heated at 95° C. for one hour under nitrogen. Benzene (275 ml) was then added and water azeotropically removed via a Dean Stark apparatus. The mixture was cooled to 0° C., seeded and stored overnight. The precipitate was collected by filtration and washed with hexane. The solid was dissolved in toluene and the resulting solution was washed with dilute ammonium hydroxide then with water. The organic phase was dried (Na$_2$SO$_4$) and evaporated. 49.8 gm of 1,3-O-benzylidenylglycerol, was recovered as a white solid.

PREPARATION VII (Preparation of compound of formula (V))

A mixture of DMSO (45 ml), glacial acetic acid (30 ml) and acetic anhydride (25 ml) was added to 1,3-O-benzylidenylglycerol (8.2 gm) and the solution was stirred for 5 days at room temperature. The solution was partially concentrated under vacuum and partitioned between dichloromethane and dilute aqueous KHCO$_3$. The organic phase was dried (Na$_2$SO$_4$) and evaporated to a yellow oil which was distilled (120°–130° C./0.5 torr) to give 9.4 gm of 1,3-O-benzylidenyl-2-O-methylthiomethylglycerol.

PREPARATION VIII (Preparation of compound of formula (VII))

A slurry of 1,3-O-benzylidenyl-2-O-methylthiomethylglycerol (1.83 gm), diacetylguanine (2.5 gm) DMSO (593 mg), AlCl$_3$ (100 mg) and dimethylformamide (10 ml) was heated for 6 hours at 80° C. The slurry was cooled and then partitioned between dichloromethane and dilute aqueous KHCO₃. The organic layer was dried (Na₂SO₄) and evaporated to a brown oil. The oil was dissolved in 100 ml of toluene/ethyl acetate (1:1). The resulting precipitate which was recovered by filtration gave 530 mg of 9-(1,3-benzylidenyldioxy-2-propoxymethyl)-$N^2$-acetylguanine.

PREPARATION IX (Preparation of 1,3-Di-O-benzylglycerol)

Sodium hydride (100 g (50% dispersion in mineral oil)), washed twice with 1 l of hexane and then dried under nitrogen, was suspended in dry dimethylformamide (1.5 l). Benzyl alcohol (400 ml) was added to the suspension at a rate (over 2 hours) to keep the temperature below 50° C. Epichlorohydrin (92.5 g) was then added dropwise over 0.5 hour. During the addition the reaction mixture was cooled with ice in order to keep the temperature below 40° C. The reaction mixture was next stirred for 16 hours at 21° C. and then for 2.5 hours at 50° C. The solvents were then removed by evaporation at reduced pressure. The oily residue was partitioned between diethyl ether (2.5 l) and water (2 l). The organic phase was washed with 2% hydrochloric acid (2 l). 1% aqueous sodium bicarbonate (2 l), and brine (1 l), dried over sodium sulfate, and concentrated to a brown oil. Distillation of the oil gave 147.8 g of 1,3-di-O-benzylglycerol (bp 170°–180° C./1 torr).

PREPARATION X (Preparation of compound of formula (VI) wherein W is a protected guanine and R′ is 2,2-dimethylpropanoyl.)

A solution of 15.5 g of $N^2$,9-diacetylguanine, 8.84 g of 1,3-bis(2,2-dimethylpropanoyloxy)-2-propoxymethylsulfinylmethane, 0.5 g of p-toluenesulfonic acid, 5.5 ml of dimethylsulfoxide in 26 ml of dimethylformamide was heated under anhydrous conditions in a 105° C. oil bath for 42 hours. The solution was cooled and dissolved in 150 ml of ethyl acetate and allowed to stand for one hour. The mixture was filtered and the precipitate was washed with 200 ml of water (3X), dried (MgSO₄), and then evaporated to dryness. The residue was chromatographed over 150 g of silica gel which was eluted with 2 l of dichloromethane, then with 4 l of 2% methanol/dichloromethane. The final 3.5 l of eluant was concentrated to a clear syrup which was dissolved in 50 ml of xylene. $N^2$-acetyl-9-[1,3-(2,2-dimethylpropanoyloxy)-2-propoxymethyl]-guanine (5.428 g) was recovered as white crystals, m.p. 192°–193° C.

PREPARATION XI (Preparation of compound of formula (III) wherein $R^1$ is benzyl and n is 0)

A mixture of 30 g 1,3-dibenzyl glycerol, 90 ml dimethyl sulfoxide, 60 ml acetic acid and 50 ml acetic anhydride was allowed to stand for 7 days. The mixture was shaken with 100 ml toluene and 200 ml water. The organic phase was separated and washed twice with 100 ml water. The organic layer was vacuum distilled to remove the solvent and the residue purified via a molecular still. The yield of crude 1,3-dibenzyl-2-methylthiomethylglycerol was 29 g which was used in subsequent reactions without further purification.

PREPARATION XII (Preparation of compound of formula (VI) wherein $R^1$ is benzyl and W is acetylguanine)

A mixture of 27 g diacetylguanine and 80 ml dimethylsulfoxide was heated to ~100° C. with stirring. To this mixture was added 45 g crude 1,3-dibenzyl-2-methylthiomethylglycerol and 0.15 g aluminum chloride. The resultant mixture was heated to ~125°–130° C. for 1½ hours and then cooled. The cooled mixture was added to 3 L water for stirring. The oily layer which forms was separated from the aqueous layers by decanting. The oil was washed with 1 L water, separated from the aqueous layer and dissolved in 4 L isopropyl acetate. The solution was heated to reflux, filtered and distilled to a volume of ~1.5 L. The solution was cooled and the crystalline product was collected by filtration, washed with isopropyl acetate and dried to yield 13.3 g of $N^2$-acetyl-9-(1,3-dibenzyloxy-2-propoxymethyl)guanine.

PREPARATION XIII

A mixture of 13.9 g $N^2$ acetyl-9-(1,3-dibenzyloxy-2-propoxymethyl)guanine, 1.3 g 20% palladium hydroxide on carbon, 140 ml methanol and 70 ml cyclohexene was refluxed under a nitrogen blanket with stirring. After 16 hours, 0.2 g 20% palladium hydroxide on carbon was added and refluxing continued for an additional 12 hours. The mixture was cooled and filtered. The resultant filter cake was slurried with 80 ml of boiling water and then filtered. The filter cake was washed with 30 ml boiling water, the filtrate vacuum distilled and the residue was slurried with 30 ml methanol. The white crystalline product collected, washed with methanol and dried to yield 6.7 g of $N^2$-acetyl-9-(1,3-dihydroxy-2-propoxymethyl)guanine.

EXAMPLE 1

(Preparation of compound of formula (I) wherein Y is hydroxy and $R^2$ is hydrogen)

A solution of $N^2$-acetyl-9-(1,3-di(2,2-dimethylpropanoyloxy-2-propoxymethyl)guanine in a mixture of concentrated ammonium hydroxide and methanol was kept at room temperature for nine days. The solution was then evaporated, leaving a white solid which was triturated with ethanol to give 51 mg of 9-(1,3-dihydroxy-2-propoxymethyl)guanine, m.p. 250° C., dec.

EXAMPLE 2

(Preparation of compound of formula (I) wherein Y is hydrogen and $R^2$ is 2,2-dimethylpropanoyl)

A solution of $N^2$-acetyl-9-[1,3-di-(2,2-dimethylpropanoyloxy)-2-propoxymethyl]guanine in 10% ammonium hydroxide in methanol was kept at room temperature for 7 hours and then evaporated. The residue was recrystallized from methanol to give 9-[1,3-di-(2,2-dimethylpropanoyloxy)-2-propoxymethyl]guanine, m.p. 230°–232° C.

EXAMPLE 3

(Preparation of compound of formula (I) wherein Y is hydroxy and $R^2$ is hydrogen)

A solution of 9-(1,3-O-benzylidenyldioxy-2-propoxymethyl)-$N^2$-acetylguanine (530 mg) in 80% aqueous acetic acid was heated at 60° C. for 2 days and then evaporated. The residue was dried by co-evaporation with ethanol (3X) and then recrystallized from hot methanol to give crystalline 9-(1,3-dihydroxypropoxymethyl)guanine (200 mg), m.p. 250° C., dec.

EXAMPLE 4

(Preparation of compound of formula (I) wherein Y is amino and $R^2$ is hydrogen)

A solution of 2-acetylamino-6-chloro-9-[1,3-di(2,2-dimethylpropanoyloxy)-2-propoxymethyl]purine (200 mg) in methanolic ammonia (15 ml) was heated in a Parr bomb at 90° C. for 18 hours. The solution was evaporated and the residue recrystallized from methanol to give 136 mg of 2,6-diamino-9-(1,3-dihydroxy-2-propoxymethyl)purine, m.p. 176°–177° C.

EXAMPLE 5

(Preparation of compound of formula (I) wherein Y is hydroxy and $R^2$ is hydrogen)

To $N^2$-acetyl-9-[1,3-di(2,2-dimethylpropanoyloxy)-2-propoxymethyl]guanine (28.0 g) in 100 ml methanol was added 5.6 g sodium methoxide in 100 ml of methanol. The mixture was heated to reflux under anhydrous conditions for 48 hours. The reaction mixture was cooled to room temperature and upon filtration under a nitrogen atmosphere 14.92 g of 9-(1,3-dihydroxy-2-propoxymethyl)-guanine sodium salt as a white powder was recovered. The powder was dissolved in 300 ml of hot water and 11 g of ammonium chloride was added. The mixture was cooled to room temperature and 12.80 g of 9-(1,3-dihydroxy-2-propoxymethyl)guanine were recovered as crystals, m.p. 250° C., dec.

What is claimed is:

1. A process for preparing a compound of the formula

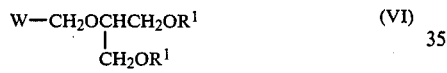

wherein each $R^1$ is a removable group and W is a protected guanine, 2-amino-6-chloropurine or 2,6-dichloropurine which comprises reacting a compound of the formula

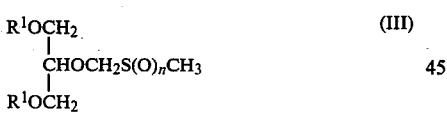

wherein $R^1$ is as defined above and n is 0 or 1 with a protected guanine, 2-amino-6-chloropurine or 2,6-dichloropurine.

2. The process of claim 1 wherein $R^1$ is a sterically hindered group.

3. The process of claim 1 wherein $R^1$ is $R^5C(O)$ wherein $R^5$ is alkyl or optionally substituted phenyl.

4. The process of claim 1 wherein $R^1$ is an optionally substituted benzyl group.

5. The process of claim 1 wherein the two $R^1$'s together is $ZZ^1C<$ wherein Z is optionally substituted phenyl and $Z^1$ is hydrogen or Z and $Z^1$ are both methyl.

6. The process of claim 1 wherein the protected purine is in admixture with a disubstituted sulfoxide.

7. The process of claim 6 wherein the disubstituted sulfoxide is dimethylsulfoxide.

8. The process of claim 7 wherein the protected purine is protected guanine.

9. The process of claim 7 wherein the protected purine is protected 2-amino-6-chloropurine.

10. The process of claim 7 wherein the protected purine is protected 2,6-dichloropurine.

11. A process for preparing a compound of the formula

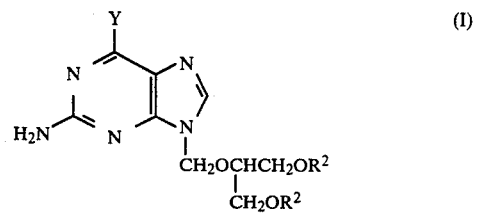

wherein Y is hydroxy or amino and $R^2$ is hydrogen or a sterically hindered acyl group which comprises (a) reacting glycerol or epichlorohydrin with a removable group precursor to form a compound of the formula

wherein each $R^1$ is a removable group;

(b) reacting the compound prepared in (a) with a disubstituted sulfoxide to form a compound of the formula

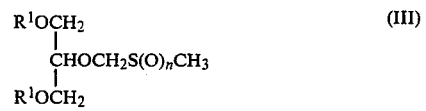

wherein $R^1$ is as defined above and n is O;

(c) optionally hydrolyzing the compound prepared in (b) wherein the two $R^1$'s together is $ZZ^1C<$ wherein Z is optionally substituted phenyl and $Z^1$ is hydrogen or Z and $Z^1$ are both methyl and then reacting with an acyl chloride of the formula $R^5C(O)Cl$ wherein $R^5$ is alkyl or optionally substituted phenyl;

(d) optionally oxidizing the sulfur atom of the compound prepared in (b) or (c) to form a compound wherein n is 1;

(e) reacting the compound prepared in (b), (c) or (d) with a protected purine selected from the group consisting of protected guanine, 2-amino-6-chloropurine and 2,6-dichloropurine to form a compound of the formula

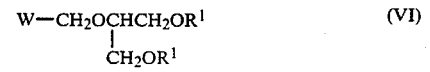

wherein $R^1$ is a removable group and W is a protected purine; and (f) contacting the compound formed in (e) with a base or an acid or with a hydrogen donor to form a compound of formula (I).

12. The process of claim 11 wherein $R^1$ is a sterically hindered group.

13. The process of claim 11 wherein $R^1$ is $R^5C(O)$ wherein $R^5$ is alkyl or optionally substituted phenyl.

14. The process of claim 11 wherein $R^1$ is an optionally substituted benzyl group.

15. The process of claim 11 wherein the two $R^1$'s together is $ZZ^1C<$ wherein Z is optionally substituted phenyl and $Z^1$ is hydrogen or Z and $Z^1$ are both methyl.

16. A process of claim 11 wherein Y is hydroxy.

17. A process of claim 11 wherein Y is amino.

18. The process of claim 11 which comprises contacting compound of formula (VI) with a base.

19. The process of claim 17 wherein the base is ammonium hydroxide, ammonia, sodium hydroxide or sodium methoxide.

20. The process of claim 19 wherein each $R^1$ is a sterically hindered acyl group or $R^5C(O)$ wherein $R^5$ is alkyl or optionally substituted phenyl.

21. The process of claim 20 which comprises contacting the compound of the formula (VI) wherein W is acyl protected guanine with a methanolic solution of ammonium hydroxide or a methanolic solution of ammonia to form the compound of formula (I) wherein Y is hydroxy.

22. The process of claim 21 wherein $R^2$ is hydrogen.

23. The process of claim 21 wherein $R^2$ is a sterically hindered acyl group.

24. The process of claim 20 which comprises contacting the compound of formula (VI) wherein W is acyl protected 2-amino-6-chloropurine with a methanolic solution of ammonium hydroxide or a methanolic solution of ammonia to form the compound of formula (I) wherein Y is amino.

25. The process of claim 24 wherein $R^2$ is hydrogen.

26. The process of claim 24 wherein $R^2$ is a sterically hindered acyl group.

27. The process of claim 20 which comprises contacting the compound of formula (VI) wherein W is acyl protected 2,6-dichloropurine with a methanolic solution of ammonium hydroxide or a methanolic solution of ammonia and further contacting the compound so formed with methanolic solution of ammonium hydroxide or a methanolic solution of ammonia under increased temperature to form the compound of formula (I) wherein Y is amino and $R^2$ is hydrogen.

28. The process of claim 11 wherein the base is sodium hydroxide.

29. The process of claim 28 which comprises contacting the compound of formula (VI) wherein W is acyl protected 2-amino-6-chloropurine with an aqueous solution of sodium hydroxide to form the compound of formula (I) wherein Y is hydroxy and $R^2$ is hydrogen.

30. The process of claim 11 which comprises contacting compound of formula (VI) with an acid.

31. The process of claim 30 wherein each $R^1$ is a sterically hindered silyl group, diphenylmethyl or a triphenylmethyl group, or the two $R^1$'s together is $ZZ^1C<$ wherein Z is optionally substituted phenyl and $Z^1$ is hydrogen or Z and $Z^1$ are both methyl.

32. The process of claim 31 wherein the acid is acetic acid.

33. The process of claim 32 which comprises contacting a compound of formula (VI) wherein W is defined in claim 11 with an aqueous solution of acetic acid and optionally with a methanolic solution of ammonium hydroxide or a methanolic solution of ammonia to form a compound of formula (I) wherein Y is as defined in claim 11.

34. The process of claim 33 wherein the compound of formula (VI) is first contacted with a methanolic solution of ammonium hydroxide or a methanolic solution of ammonia.

35. The process of claim 34 wherein the compound of formula (VI) is first contacted with an aqueous solution of acetic acid.

36. The process of claim 11 wherein the protected purine is in admixture with a disubstituted sulfoxide.

37. The process of claim 36 wherein the disubstituted sulfoxide is dimethylsulfoxide.

38. The process of claim 37 wherein the protected purine is protected guanine.

39. The process of claim 37 wherein the protected purine is protected 2-amino-6-chloropurine.

40. The process of claim 37 wherein the protected purine is protected 2,6-dichloropurine.

41. The process of claim 11 wherein compound of formula (VI) is contacted with a hydrogen donor to form a compound of formula (I) wherein $R^2$ is hydrogen.

42. The process of claim 41 wherein each $R^1$ is an optionally substituted benzyl group.

43. The process of claim 42 wherein compound of formula (VI) is contacted with hydrogen in the presence of a hydrogenation catalyst.

44. The process of claim 43 wherein the hydrogenation catalyst is palladium-on-carbon.

45. The process of claim 43 which further comprises contacting the compound formed in claim 43 with a base or an acid.

46. The process of claim 45 which comprises contacting compound of formula (VI) with a base.

47. The process of claim 46 wherein the base is ammonium hydroxide, ammonia, sodium hydroxide or sodium methoxide.

48. The process of claim 45 which comprises contacting compound of formula (VI) with an acid.

49. The process of claim 48 wherein the acid is acetic acid.

50. The process of claim 41 wherein the hydrogen donor is cyclohexene or 1,4-cyclohexadiene.

51. The process of claim 50 wherein the hydrogen donor is cyclohexene.

52. A process for preparing a compound of the formula

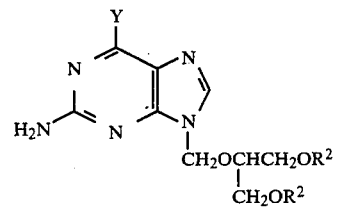

wherein Y is hydroxy or amino and $R^2$ is hydrogen or a sterically hindered acyl group which comprises (a) reacting a compound of the formula

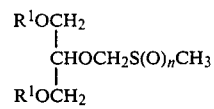

wherein $R^1$ is a removable group and n is 0 or 1 with a protected purine selected from the groups consisting of protected guanine, 2-amino-6-chloropurine and 2,6-dichloropurine to form a compound of the formula

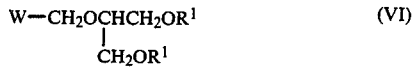

wherein $R^1$ is as defined above and W is a protected purine; and (b) contacting the compound formed in (a) with a base or an acid or with a hydrogen donor to form a compound of formula (I).

53. The process of claim 52 wherein $R^1$ is a sterically hindered group.

54. The process of claim 52 wherein $R^1$ is $R^5C(O)$ wherein $R^5$ is alkyl or optionally substituted phenyl.

55. The process of claim 52 wherein $R^1$ is an optionally substituted benzyl group.

56. The process of claim 52 wherein the two $R^1$'s together is $ZZ^1C<$ wherein Z is optionally substituted phenyl and $Z^1$ is hydrogen or Z and $Z^1$ are both methyl.

57. A process of claim 52 wherein Y is hydroxy.

58. A process of claim 52 wherein Y is amino.

59. The process of claim 52 which comprises contacting compound of formula (VI) with a base.

60. The process of claim 59 wherein the base is ammonium hydroxide, ammonia, sodium hydroxide or sodium methoxide.

61. The process of claim 60 wherein each $R^1$ is a sterically hindered acyl group or $R^5C(O)$ wherein $R^5$ is alkyl or optionally substituted phenyl.

62. The process of claim 61 which comprises contacting the compound of the formula (VI) wherein W is acyl protected guanine with a methanolic solution of ammonium hydroxide or a methanolic solution of ammonia to form the compound of formula (I) wherein Y is hydroxy.

63. The process of claim 62 wherein $R^2$ is hydrogen.

64. The process of claim 62 wherein $R^2$ is a sterically hindered acyl group.

65. The process of claim 61 which comprises contacting the compound of formula (VI) wherein W is acyl protected 2-amino-6-chloropurine with a methanolic solution of ammonium hydroxide or a methanolic solution of ammonia to form the compound of formula (I) wherein Y is amino.

66. The process of claim 65 wherein $R^2$ is hydrogen.

67. The process of claim 65 wherein $R^2$ is a sterically hindered acyl group.

68. The process of claim 61 which comprises contacting the compound of formula (VI) wherein W is acyl protected 2,6-dichloropurine with a methanolic solution of ammonium hydroxide or a methanolic solution of ammonia and further contacting the compound so formed with methanolic solution of ammonium hydroxide or a methanolic solution of ammonia under increased temperature to form the compound of formula (I) wherein Y is amino and $R^2$ is hydrogen.

69. The process of claim 60 wherein the base is sodium hydroxide.

70. The process of claim 69 which comprises contacting the compound of formula (VI) wherein W is acyl protected 2-amino-6-chloropurine with an aqueous solution of sodium hydroxide or a methanolic solution of ammonia to form the compound of formula (I) wherein Y is hydroxy and $R^2$ is hydrogen.

71. The process of claim 52 which comprises contacting compound of formula (VI) with an acid.

72. The process of claim 71 wherein each $R^1$ is a sterically hindered silyl, diphenylmethyl or triphenylmethyl or the two $R^1$'s together are $ZZ^1C<$ wherein Z is optionally substituted phenyl and $Z^1$ is hydrogen or Z and $Z^1$ are both methyl.

73. The process of claim 72 wherein the acid is acetic acid.

74. The process of claim 73 which comprises contacting a compound of formula (VI) wherein W is defined in claim 52 with an aqueous solution of acetic acid and optionally with a methanolic solution of ammonium hydroxide or a methanolic solution of ammonia to form a compound of formula (I) wherein Y is as defined in claim 52.

75. The process of claim 74 wherein the compound of formula (VI) is first contacted with a methanolic solution of ammonium hydroxide or a methanolic solution of ammonia.

76. The process of claim 74 wherein the compound of formula (VI) is first contacted with an aqueous solution of acetic acid.

77. The process of claim 52 wherein compound of formula (VI) is contacted with a hydrogen donor to form a compound of formula (I) wherein $R^2$ is hydrogen.

78. The process of claim 77 wherein each $R^1$ is an optionally substituted benzyl group.

79. The process of claim 78 wherein compound of formula (VI) is contacted with hydrogen in the presence of a hydrogenation catalyst.

80. The process of claim 79 wherein the hydrogenation catalyst is palladium-on-carbon.

81. The process of claim 79 which further comprises contacting the compound formed in claim 79 with a base or an acid.

82. The process of claim 81 which comprises contacting the compound formed in claim 79 with a base.

83. The process of claim 82 wherein the base is ammonium hydroxide, ammonia, sodium hydroxide or sodium methoxide.

84. The process of claim 79 which comprises contacting the compound formed in claim 79 with an acid.

85. The process of claim 84 wherein the acid is acetic acid.

86. The process of claim 77 wherein the hydrogen donor is cyclohexene or 1,4-cyclohexadiene.

87. The process of claim 86 wherein the hydrogen donor is cyclohexene.

88. The process of claim 52 wherein the protected purine is in admixture with a disubstituted sulfoxide.

89. The process of claim 88 wherein the disubstituted sulfoxide is dimethylsulfoxide.

90. The process of claim 89 wherein the protected purine is protected guanine.

91. The process of claim 89 wherein the protected purine is protected 2-amino-6-chloropurine.

92. The process of claim 89 wherein the protected purine is protected 2,6-dichloropurine.

* * * * *